United States Patent [19]

Reuveni

[11] Patent Number: 4,682,291
[45] Date of Patent: Jul. 21, 1987

[54] NOISE ARTIFACTS REDUCTION

[75] Inventor: Asher Reuveni, Natanya, Israel

[73] Assignee: Elscint Ltd., Haifa, Israel

[21] Appl. No.: 665,047

[22] Filed: Oct. 26, 1984

[51] Int. Cl.$^4$ .................. G06F 15/42; G01T 1/29; G01N 23/04

[52] U.S. Cl. .................. 364/414; 378/901; 358/213.15

[58] Field of Search .......... 369/414; 378/901; 358/213

[56] References Cited

U.S. PATENT DOCUMENTS

| Re. 30,947 | 5/1982 | Boyd et al. | 250/445 |
|---|---|---|---|
| 4,075,492 | 5/1982 | Boyd et al. | 250/445 |
| 4,217,641 | 8/1980 | Naparstek | 364/414 |
| 4,352,020 | 9/1982 | Horiba et al. | 378/13 |
| 4,570,224 | 2/1986 | Shimoni et al. | 364/414 |
| 4,574,311 | 3/1986 | Resnikoss | 358/213 |

OTHER PUBLICATIONS

"A Simple Computational Method for Reducing Streak Artifacts in CT Images", G. Henrich, in *Computed Tomography*, vol. 4, 1981.

*Primary Examiner*—Jerry Smith
*Assistant Examiner*—Charles B. Meyer
*Attorney, Agent, or Firm*—Sandler & Greenblum

[57] ABSTRACT

Equipment and methods improving the quality of a tomograph are presented for rearranging divergent beam derived data into parallel data. The equipment and method perform uniform noise distribution interpolation either in the reordering phase or in the rebinning phase or in both phases. When the uniform noise distribution interpolation is employed noise streak artifacts, normally present in images, virtually disappear.

18 Claims, 13 Drawing Figures

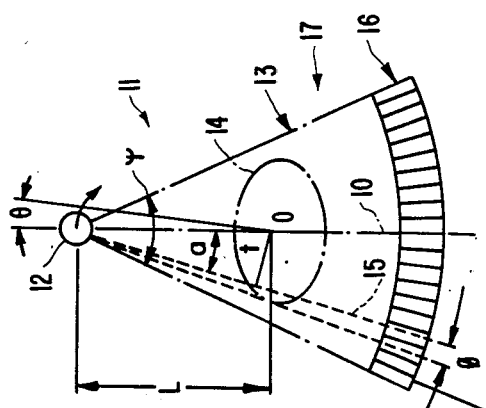
FIG. 1.
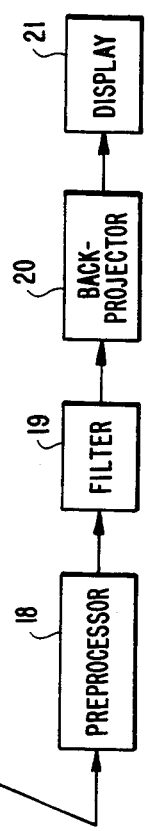
FIG. 2.
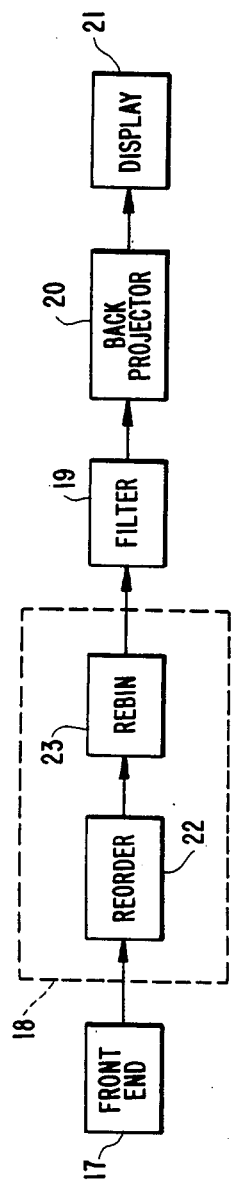

FIG. 9.
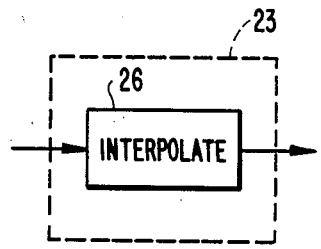
FIG. 10.
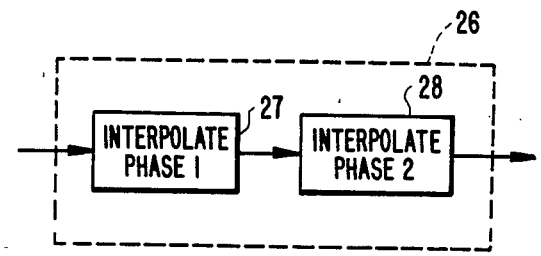
FIG. 11.
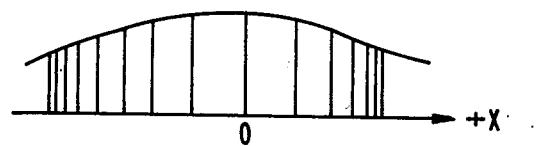
FIG. 12.
$$\begin{array}{c|ccc} & I(j-1) & I(j) & I(j+1) \\ \hline & t(j-1) & t(j) & t(j+1) \end{array}$$
$$\begin{array}{c|cc} & 0(i-1) & 0(i) \\ \hline & & t \end{array}$$
FIG. 13.
$$\begin{array}{c|ccc} & I(j-1) & I(j) & I(j+1) \\ \hline & t(j-1) & t(j) & t(j+1) \end{array}$$
$$\begin{array}{c|ccc} & Q(K-1) & Q(K) & Q(K+1) \\ \hline & t(K-1) & t(K) & t(K+1) \end{array}$$
$$\begin{array}{c|ccc} 0(i-1) & 0(i) & 0(i+1) \\ \hline t(i-1) & t(i) & t(i+1) \end{array}$$

NOISE ARTIFACTS REDUCTION

FIELD OF THE INVENTION

This invention relates to rearranging divergent beams used in tomography, and more particularly to reducing noise artifacts caused by the rearrangement.

BACKGROUND OF THE INVENTION

Various artifacts plague the medical images obtained by CT scanners. The scientists and engineers who develop such equipment are continuously attempting to reduce the image artifacts. An example of such artifacts is the polychromatic artifact indentified by cupping and streaks in images. An example of a system for minimizing artifacts is shown in U.S. Pat. No. 4,217,641 which uses an iterative post-reconstruction method to reduce the level of the artifacts. As another example, there is the paper entitled "A Simple Computational Method for Reducing Streak Artifacts in CT Images", by G. Henrich, in Computed Tomography, Vol. 4, 1981 which describes an algorithm that can be used to remove streaks such as those caused by partial volume artifacts. Ring artifacts in rotational CT scanners are well known. U.S. Pat. No. 4,352,020 uses a calibration method to reduce such artifacts.

U.S. Pat. Nos. RE. 30,947 and 4,075,492 teach reordering the divergent rays of a fan beam CT scanner into parallel rays. However the spacings between the reordered rays are not laterally equal. This causes "cupping" artifacts. To remove these artifacts the RE 30947 Patent presents an interpolation method that generates parallel projections of equal spacing between samples from unequally spaced reordered projections. U.S. Pat. No. 4,570,224 which issued on Feb. 11, 1986 and is assigned to the assignee of this invention, gives additional methods for reducing the cupping artifacts by using other interpolation techniques.

A problem encountered with both the above interpolation methods is that while they do succeed in reducing the cupping artifacts the interpolation methods produce structured noise in the reconstructed images. The noise has the form of partial streaks tangent to several circles on the image, as if caused by a rotational noise sprinkler. As a special case, these streaks can be radial (when the circle is of a very small radius).

The cause of the artifact generally is that the signal output from each detector contains data and noise. Since the reconstruction system is linear the effect of the input noise can be analyzed while the data is ignored. Suppose an interpolated (output) sample is calculated from two input samples by linear interpolation, the noise of the output sample depends on the interpolation coefficients.

The noise is attenuated, for example, by a factor of 0.7071 (when both coefficients are 0.5) and by a factor of 1 (when one coefficient is 1 and the other is 0). As a consequence of the interpolation, the interpolated data (the parallel projection) will have points of "Low Noise" (corresponding to the attenuation factor 0.7071), and points of "High Noise" (corresponding to the attenuation factor (1) in which the noise level is not changed. After filtration and back-projection, streaks of noise tangent to a circle corresponding to "High Noise" points appear in the reconstructed image.

Similar noise artifacts can occur when interpolation is performed between samples of the same detector; i.e, vertical interpolation, as distinguished from horizontal interpolation where the interpolation is between the samples of a projection. In CT scanners such vertical interpolations have been employed as a step in reordering divergent projections to (unequally spaced) parallel projections. See, for example, the book "Image Reconstruction from Projections", by Gabor T. Herman, Academic Press, 1980. Another case where vertical interpolation has been used is when the reordered projections are not perfectly parallel such as for example, in Dual Focal Spot Scanners (see Patent application Ser. No. 518,121 filed on July 7, 1983 and assigned to the assignee of this invention).

In all the above examples of the use of interpolation, if the interpolation coefficients used for calculating samples are different for adjacent samples in the obtained projection, but are identical for the same sample in all (or in part of) the projections, the noise is attenuated by different factors. Hence, the projections will contain non-uniform noise which can cause artifacts in the image as explained earlier. Accordingly there is a need for systems and/or method for minimizing noise artifacts generated when interpolation methods change normally uniform noise distribution to non-uniform noise distribution.

SUMMARY OF PRESENT INVENTION

Accordingly, an object of the present invention is to provide for rearranging divergent beam derived data without significantly changing the noise distribution of the data with respect to the input. Such CT images from the rearranged data have uniform noise distribution and do not suffer from structured noise. The inventive method includes the steps of:

directing divergent beams of penetrating radiation through a body being examined from source means on one side of said body, angularly displacing the divergent beams relative to the body, detecting radiation that has passed through the body at a number of angularly spaced positions to derive sets of detected radiation data representative of a plurality of angularly spaced shadowgrams indicative of the absorption of the radiation by different portions of the body, reordering the sets of detected radiation data from sets of data corresponding to divergent projections to sets of data corresponding to parallel projections, rebinning at least a portion of the sets of data corresponding to said parallel projections, the rebinning step including the step of using a uniform noise distribution interpolation to form a new set of parallel projections, and combining the non-rebinned portions and the rebinned portions to form a tomographic image.

The lateral spacing of the rebinned set of parallel projections can be according to any technique. For example, it can be equal lateral spacing (as in U.S. Pat. No. Re. 30,947) or unequal lateral spacing (as in the above noted U.S. Pat. No. 4,570,224).

A feature of the invention includes a uniform noise distribution interpolation step as part of the reordering step. This reordering interpolation is desirable for certain types of scanners.

In a preferred embodiment the uniform noise interpolation step includes attenuation of the noise in places where normal interpolation does not change the noise level (High Noise points). This is preferably achieved by including more input points in computing an output sample than in other techniques (e.g., 3 point interpolation instead of 2 point interpolation). Equivalently, the interpolation can be performed in two phases from practical considerations.

BRIEF DESCRIPTION OF THE DRAWINGS

Other objects, features and advantages of the present invention will become more apparent from the description that follows taken in conjunction with the accompanying drawings showing apparatus used to describe and to implement the invention, wherein:

FIG. 1 is a pictorial block diagram showing of a CT scanner using a divergent ray source and equipped to perform the inventive method;

FIGS. 2–5 show different embodiments of details of the block diagram of FIG. 1;

FIGS. 6–10 give additional details of the blocks of FIGS. 2–5;

FIG. 11 is a diagram showing the lateral spacing between samples in a parallel projection after reordering; and FIGS. 12–13 show the lateral coordinates of samples before interpolation and after interpolation.

DETAILED DESCRIPTION

Figure 3:
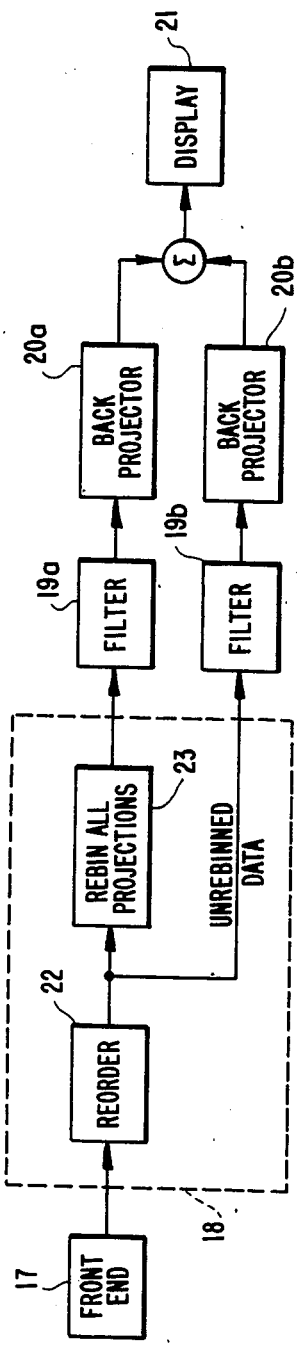

A typical fan or divergent beam source 12 is shown in the CT scanner equipment 11 of FIG. 1. The divergent radiation beam shown as 13 goes through a body 14. The beam is angularly displaced relative to the body by moving the source 12. Shadowgram data is taken in angular steps shown as the angle "theta" in the example.

In a preferred embodiment the radiation that has passed through the body is detected by an array of angularly spaced detectors 16 located within the angle "psi" subtended by the divergent beam. However, the array need not be restricted to the angle "psi" for purposes of the invention.

This condition provides for an embodiment in which different sets of detectors are used for each fan-beam projection. The source 12, detecters 16 and associated equipment are often referred to as the front-end 17 of the CT system.

The detectors are used to derive sets of angularly spaced shadowgrams which indicate the absorption of radiation by different parts of the body. Equivalently the vertex of the fan can be either the source of radiation or individual detectors.

Figure 4:
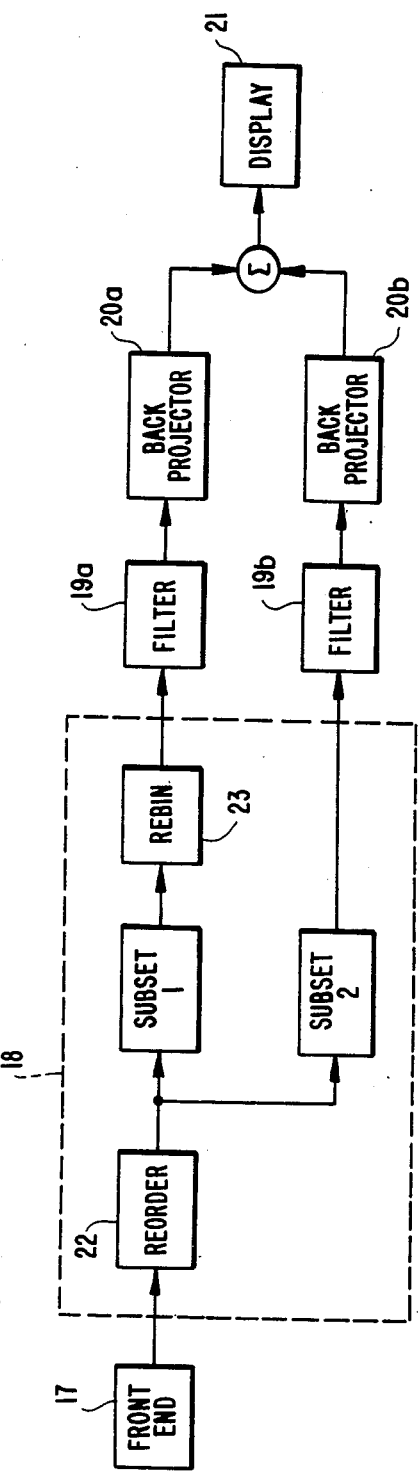
Figure 5:
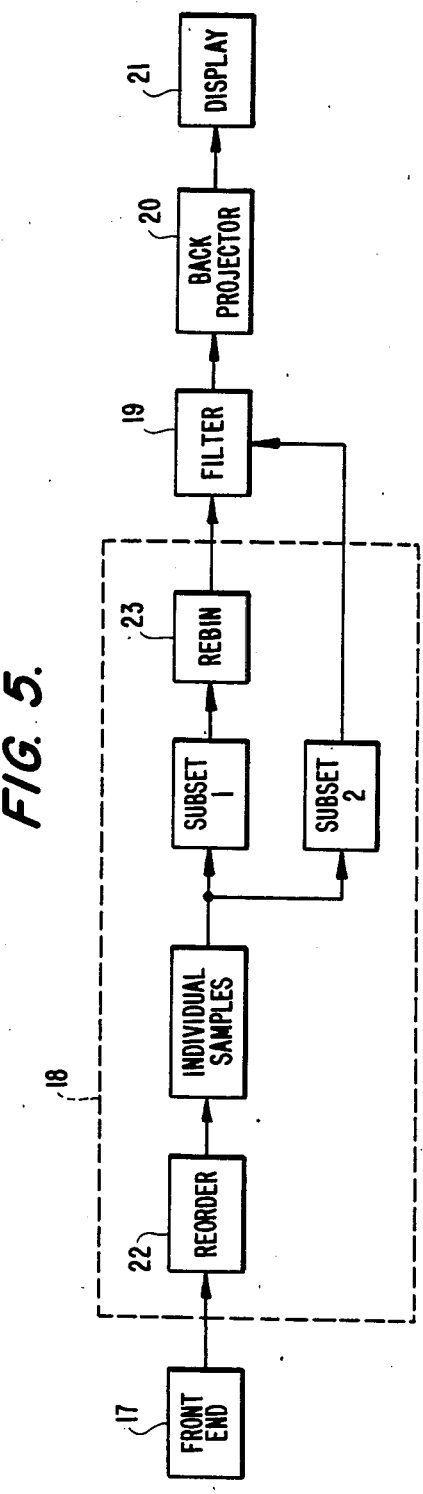

As can be seen from FIG. 1, the sets of detected radiation data are operated on to provide a display image. More particularly the data may be preprocessed in a pre-processor 18, filtered by a filter 19 and back-projected by a back-projector 20. The image obtained is displayed by the display unit 21. There may be several variations in the implementation of blocks 18–20 of FIG. 1. FIG. 2 depicts the implementation described in U.S. Pat. No. RE. 30,947. FIGS. 3–5 depict the implementation described in U.S. Pat. No. 4,570,224.

Figure 8:
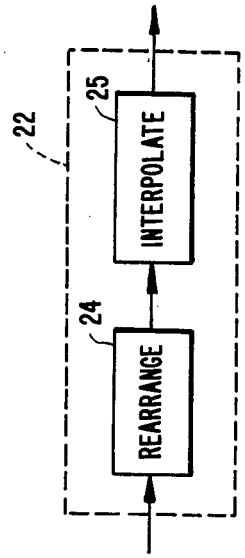
Figure 7:
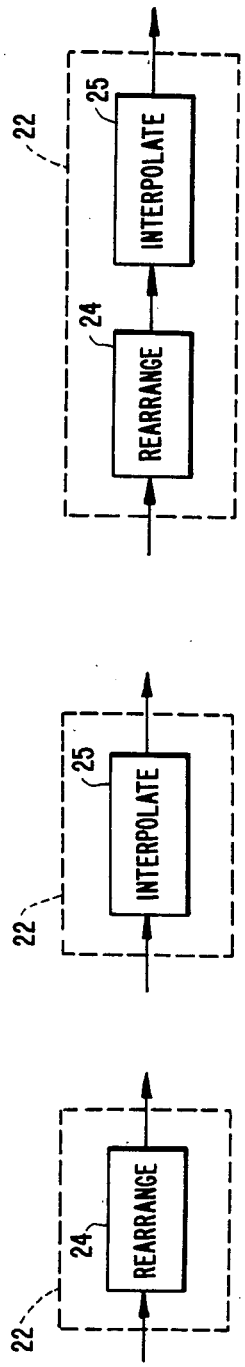
Figure 6:
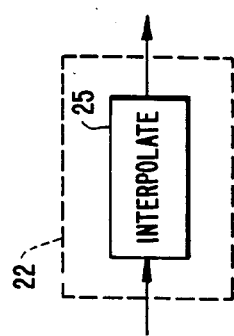

The detailed explanations given in both the reissue patent and the patent with respect to the exact behaviour of these blocks will not be repeated. Only explanations needed for understanding the invention; i.e, the blocks for accomplishing and using the invention are described herein in detail. The sets of detected radiation data are reordered as shown at 22 in preprocessor 18 to, among other things, change the fan-beam projections to parallel projections. The reordering is accomplished in any manner well known to those skilled in the art. The reordering can be implemented by simply rearranging the data as indicated at 24 (FIG. 6) and as explained in U.S. Pat. No. RE. 30,947. However, depending on the CT scanner this reordering may require the use of interpolation, as indicated at 25, of vertical data sets either to perform the whole reordering step (FIG. 7) or to complement the rearranging (FIG. 8).

Where such interpolation is used, the inventive system and method can be implemented as explained in detail further herein to prevent noise artifacts. The reordered data provides projections which have samples corresponding to rays that are parallel, but the lateral spacing between the rays is unequal. The spacing in the preferred embodiment generally follows a cosine function, such as shown in FIG. 11.

In one method (FIG. 2), all parallel projections are rebinned as indicated at 23 to form equally spaced projections, or in other methods (FIGS. 3–5) all or part of the parallel projections are rebinned as indicated at 23 to form unequally spaced projections. All above rebinning operations are horizontal interpolations indicated at 26 (FIG. 9). The various spacing equations are explained in U.S. Pat. No. RE. 30,947 (equally spaced), and U.S. Pat. No. 4,570,224. Each of these interpolations is replaced by the inventive interpolation indicated at 26 to prevent noise artifacts. While the following explanation is given in terms of horizontal interpolations the same system can be used for all interpolations.

For a clearer understanding of the invention the process by which interpolation causes noise artifacts is explained in detail. Consider FIG. 12; suppose the equation for generating output sample i O (i) from two input samples I(j) and I(j+1) is:

$$O(i) = A(i)*I(j) + B(i)*I(j+1) \tag{1}$$

where A and B are the interpolation coefficients, which are functions of (i). Let the noise standard deviation of input sample j be SI(j) and of output sample i be SO(i). Since samples j and j+1 are independent:

$$SO(i)^2 = A(i)^2 * SI(j)^2 + B(i)^2 * SI(j+1)^2 \tag{2}$$

If the noise associated with each detector has the same standard deviation SI (the usual case), then:

$$SO(i) = SI*SQRT(A(i)^2 + B(i))^2 \tag{3}$$

If $A(i) + B(i) = 1$, as in normal 2 point interpolation, the multiplicand of SI varies between SQRT (0.5) i.e., (0.7071) and SQRT (1) i.e, (1) along a projection. As a consequence of the interpolation, the interpolated data (the parallel projection) will have points of "Low Noise" (corresponding to the 0.7071) and points of "High Noise" (corresponding to the 1) in which the noise level is not changed. After filtration and back-projection, streaks of noise tangent to a circle corresponding to High Noise points appear in the reconstructed image.

Therefore to prevent the interpolation induced noise artifacts, interpolation that provides uniform noise distribution should be used. An explanation of the mathematical basis for such uniform noise distribution interpolation and the means and steps of accomplishing the uniform noise distribution interpolation follows.

Consider the sampling intervals of the unrebinned data. In FIG. 1, the straight line 10 passing through the vertex of the divergent fan and the origin of the scan is called the "center line". Line 15 is a ray connecting the source and a detector. Let "a" be the angle that is subtended by this ray and the "center line". Let "L" denote the distance from the origin, "O", of the scan system to the vertex of the fan. Let "t" be the perpendicular distance from "O" to line 15. The value t is given by:

$$t = L * \sin(a) \tag{4}$$

In a real system there exists a finite number of discrete rays. Assume that there are "N" rays. The angle of each ray is denoted as "a(j)" where j = 1, 2, ... N. In a preferred embodiment, the angle between adjacent rays is a constant. Thus:

$$a(j+1) - a(j) = \text{``d\_a''} \tag{5}$$

where "d_a" is a constant. The samples of the parallel projections that are obtained after reordering are located at the positions given by:

$$t(j) = L * \sin(a(j)) \tag{6}$$

where is is assumed, for the purposes of this example, that the angle between source positions is also given by "d_a."

Now, using FIGS. 12 and 13 examine how an output sample O(i) is generated from the input samples I(j) in a projection. Let the lateral coordinate of output sample i be t, and the coordinates of input sample I(j) be t(j) (see FIG. 12). In normal two point interpolation the output sample O(i) is obtained as follows:

$$O(i) = A * I(j) + B * I(j+1) \tag{7}$$

A and B are found from physical considerations. For example:

$$A = (t(j+1) - t)/(t(j+1) - t(j)); B = 1 - A \tag{8}$$

In some cases 3 point interpolation is used as shown in FIG. 13, then:

$$O(i) = A * I(j-1) + B * I(j) + C * I(j+1) \tag{9}$$

where A + B + C = 1. A, B and C are found from physical considerations.

In the inventive scheme, unlike prior art, interpolation noise considerations are included in the calculations of interpolation coefficients. The inventive system uses an additional interpolation point. As a concrete example, the interpolation computation is shown for the case where the original interpolation is a two point interpolation, and the inventive method uses three point interpolation.

However, the invention is not limited to interpolations originally accomplished using two points but can be easily modified to handle interpolation originally accomplished using more than two points. Given the coordinate t of output sample i, three points I(j−1), I(j), I(j+1) with corresponding coordinates t(j−1), t(j), t(j+1) are selected (see FIG. 12). The selection is made such that input point j is the closest to output point i along the t coordinate, i.e.:

$$(t(j) + t(j-1))/2 <= t(j) <= (t(j) + t(j+1))/2 \tag{10}$$

The output O(i) is computed form:

$$O(i) = A * I(j-1) + B * I(j) + C * I(j+1) \tag{11}$$

The following equations and constraints must be satisfied:

$$A + B + C = 1 \tag{12}$$

$$A * t(j-1) + B * t(j) + C * t(j+1) = t \tag{13}$$

$$A^2 + B^2 + C^2 = K \tag{14}$$

$$A, B, C >= 0 \tag{15}$$

$$A, B, C <= 1 \tag{16}$$

From 12 and 13 we get $$A*(t(j-1) - t(j)) + C*(t(j+1) - t(j)) = t - t(j) \tag{17}$$

$$C - A*(t(j) - t(j-1))/(t(j+1) - t(j)) = = (t - t(j))/(t(j+1) - t(j)) = X \tag{18}$$

Equation 18 defines a new variable X. If R is defined as:

$$R = (t(j) - t(j-1))/(t(j+1) - t(j)) \tag{19}$$

Then:

$$C = A * R + X \tag{20}$$

From 12, 14 and 20:

$$(R^2 + R + 1)*A^2 + (X*(2*R+1) - (R+1))*A + (X^2 + (1-X)^2 - K)/2 = 0 \tag{21}$$

A can be found from 21, C can be found from 20 and B from 12. Out of the two solution sets, the solution with maximal B is selected.

For rotational CT scanners R is the ratio of two cosines (as can be shown using 6) and is very close to 1 (a typical deviation is less than 0.1%). In vertical interpolation problems R = 1. If we use R = 1, we get X ≤ 0.5. For this case 21 becomes:

$$3*A^2 + (3*X - 2)*A + (X^2 + (1-X)^2 - K)/2 = 0 \tag{22}$$

It can be shown that real solutions exist if K >= 11/24. Also, constraints (15) and (16) are satisfied for K < 0.5. The largest possible K is used. If, for example, K = 0.4999 is used this corresponds to attenuation of the noise by a factor of 0.7070.

Note that as a side effect of achieving uniform noise distribution, at some points along the projection there is some loss of spatial resolution. Thus, a combination of the original output O1 (i) (e.g, from 7 or 9) and the uniform noise distribution output O2 (from 11) can be used. For example:

$$O(i) = D * O_1(i) + E * O_2(i) \tag{23}$$

where D + E = 1, and D, E >= 0. The coefficients can thus be tuned depending on the noise level in the specific CT scanner.

In some cases two point interpolation is preferable to three point interpolation. For example, if hardware supporting two point intepolation exists. The three point interpolation can be implemented using a two phase two point interpolation system (see FIG. 10). Thus, O(i) = A*I(j−1) + B*I(j) + C*I(j+1) can be replaced by:

$$P(i) = W*I(j-1) + (1-W)*I(j) \tag{24}$$

$$Q(i) = W*I(j) + (1-W)*I(j+1) \tag{25}$$

$$O(i) = V*P(i) + (1-V)*Q(i) \tag{26}$$

Then:

$$O(i) = V*W*I(j-1) + (V*(1-W) + (1-V)*W)*I(j) + (1-V)*(1-W)*I(j+1) \tag{27}$$

Thus:

$$A = V*W \tag{28}$$

$$C = (1-V)*(1-W) \tag{29}$$

$$B = V*(1-W) + (1-V)*W \tag{30}$$

From 28 and 29:

$$W^2 + (C-A-1)*W + A = 0 \tag{31}$$

From which W is found. V is found from 28.

In the two phase interpolation (FIG. 10) the input projection samples are I(j), the output projection samples are O(i), and there is an intermediate projection with samples Q(k) (see FIG. 13). The coordinates of the intermediate samples Q(k) can be calculated as explained earlier. However, approximations to the uniform noise distribution interpolation (or improvements to the noise distribution obtained by normal interpolation) can be achieved by choosing the coordinates of the intermediate points by physical considerations. For example, if the input coordinates are given by equation 6, an improvement can be achieved if the intermediate samples coordinates t(k) are given by:

$$t(k) = C1*L*\sin(C2*a(k))$$

for appropriate constants C1 and C2.

While this invention has been described using exemplary embodiments, it should be understood that the description is made by way of example only and not as a limitation on the scope of the invention.

What is claimed is:

1. A method for rearranging divergent beam derived data to obtain tomographic images with uniform noise distribution, the method including the steps of:
    directing divergent beams of penetrating radiation through a body being examined from source means on one side of said body,
    angularly displacing the divergent beams relative to the body,
    detecting radiation that has passed through the body at a number of angularly spaced positions to derive sets of detected radiation data representative of a plurality of angularly spaced shadowgrams indicative of the absorption of the radiation by different portions of the body,
    reordering the sets of detected radiation data from sets of data corresponding to divergent projections to sets of data corresponding to parallel projections,
    said reordering step including the step of interpolating using uniform noise distribution interpolation,
    rebinning at least a portion of the sets of data corresponding to said parallel projections to form another set of parallel projections, and
    using the rebinned data in the formation of a displayed image.

2. The method of claim 1 wherein the reordering step is performed by first rearranging the data and then using the uniform noise distribution interpolation.

3. The method of claim 1 wherein the reordering step includes employing methods other than uniform noise distribution interpolation and the rebinning step includes using the uniform noise distribution interpolation.

4. The method of claim 1 wherein the rebinning step includes using uniform noise distribution interpolation.

5. The method of claims 1, 2, 3 or 4 wherein said uniform noise distribution interpolation step includes employing a conventional interpolation with at least an additional interpolation point.

6. The method of claim 5 wherein said uniform noise distribution interpolation step includes using three point interpolation.

7. The method of claim 5 wherein said uniform noise distribution interpolation includes using two phase two point interpolation.

8. A method for rearranging divergent beam derived data to obtain tomographic images with uniform noise distribution, the method including the steps of:
    (a) directing divergent beams of penetrating radiation through a body being examined from source means on one side of said body;
    (b) angularly displacing the divergent beams relative to the body;
    (c) detecting radiation that has passed through the body at a number of angularly spaced positions to derive sets of detected radiation data representative of a plurality of angularly spaced shadowgrams indicative of the absorption of the radiation by different portions of the body;
    (d) reordering the sets of detected radiation data from sets of data corresponding to divergent projections to sets of data corresponding to parallel projections;
    (e) said reordering step including the step of interpolating using uniform noise distribution interpolation;
    (f) said uniform noise distribution interpolation including using two phase two point interpolation;
    (g) rebinning at least a portion of the sets of data corresponding to said parallel projections to form another set of parallel projections, wherein in the rebinning step, the coordinates t(k) of intermediate samples are given by:

$$t(k) = C1*L*\sin(C2*a(k));$$

and
    (h) using the rebinned data in the formation of displayed image.

9. The method of claims 1, 2, 3, 4, or 8 wherein:
    the reordering step includes combining two contributions, one that employs methods other than uniform noise distribution interpolation, and one that employs uniform noise distribution interpolation, and wherein
    the rebinning step combines two contributions one that employs methods other than uniform noise distribution interpolation and one that employs uniform noise distribution interpolation.

10. Equipment for rearranging divergent beam derived data to obtain tomographic images with uniform noise distribution, said equipment comprising:
  (a) means for directing divergent beams of penetrating radiation through a body being examined from source means on one side of said body;
  (b) means for angularly displacing the divergent beams relative to the body;
  (c) means for detecting radiation that has passed through the body at a number of angularly spaced positions to derive sets of detected radiation data representatives of a plurality of angularly spaced shadowgrams indicative of the absorption of the radiation by different portions of the body;
  (d) means including uniform noise distribution means for reordering the sets of detected radiation data from sets of data corresponding to divergent projections to sets of data corresponding to parallel projections;
  (e) means for rebinning at least a portion of the sets of data corresponding to said parallel projections, to form another set of parallel projections; and
  (f) means for using said another set of parallel projections in the formation of a displayed image.

11. The equipment of claim 10 wherein the reordering means include rearranging means and uniform noise distribution means.

12. The equipment of claim 10 wherein the means for uniform noise distribution is included in the rebinning means instead of in the reordering means.

13. The equipment of claims 10 wherein the means for uniform noise distribution is included in the reordering means and in the rebinning means.

14. The equipment of claims 10, 11, 12 or 13 wherein said uniform noise distribution means comprises interpolation means for performing a conventional interpolation with at least an additional interpolation point.

15. The equipment of claim 14 wherein the interpolation means comprises means for performing three point interpolation.

16. The equipment of claim 14 wherein said interpolation means comprises means for performing two phase two point interpolation.

17. Equipment for rearranging divergent beam derived data to obtain tomographic images with uniform noise distribution, said equipment comprising:
  (a) means for directing divergent beams of penetrating radiation through a body being examined from source means on one side of said body;
  (b) means for angularly displacing the divergent beams relative to the body;
  (c) means for detecting radiation that has passed through the body at a number of angularly spaced positions to derive sets of detected radiation data representative of a plurality of angularly spaced shadowgrams indicative of the absorption of the radiation by different portions of the body;
  (d) means including uniform noise distribution means for reordering the sets of detected radiation data from sets of data corresponding to divergent projections to sets of data corresponding to parallel projections;
  (e) said uniform noise distribution means including interpolation means for performing uniform noise interpolation;
  (f) rebinning means for rebinning at least a portion of the sets of data corresponding to said parallel projections to form another set of parallel projections; and
  (g) said rebinning means including means for providing intermediate sample coordinates T (k) given by:

$$t(k) = C1 * L * \sin(C2 * a(k)).$$

18. The equipment of claims 10, 11, 12, 13, or 17 wherein:
  the reordering means combines special interpolation means providing uniform noise distribution interpolation and regular interpolation, and wherein
  the rebinning means combines special interpolation means providing uniform noise distribution interpolation and regular interpolation.

* * * * *